United States Patent [19]

Deyloff

[11] Patent Number: 4,468,456
[45] Date of Patent: Aug. 28, 1984

[54] MEDIUM FOR DIFFERENTIATING STREPTOCOCCUS MUTANS

[75] Inventor: John L. Deyloff, Dover, N.J.

[73] Assignee: Warner-Lambert Company, Morris Plains, N.J.

[21] Appl. No.: 362,805

[22] Filed: Mar. 29, 1982

[51] Int. Cl.$^3$ ............... C12Q 1/14; C12Q 1/04; C12N 1/20; C12R 1/46
[52] U.S. Cl. .................... 435/36; 435/34; 435/253; 435/885
[58] Field of Search .............. 435/29, 34, 36, 101, 435/103, 253, 885

[56] References Cited

U.S. PATENT DOCUMENTS

| | | | |
|---|---|---|---|
| 3,890,200 | 6/1975 | Jordan et al. | 435/885 |
| 3,935,067 | 1/1976 | Thayer | 435/253 |
| 4,102,743 | 7/1978 | Yokobayashi et al. | 435/101 |
| 4,397,944 | 8/1983 | Komura et al. | 435/34 |

FOREIGN PATENT DOCUMENTS

| | | | |
|---|---|---|---|
| 0055260 | 4/1980 | Japan | 435/34 |
| 0032998 | 4/1981 | Japan | 435/34 |

OTHER PUBLICATIONS

Ducker et al., "Comparative Effects of the Substance-Sweetners Glucose, Sorbitol, Sucrose, Xylitol, and Trichlosucrose", Arch. Oral Biol. 24(12) (1979), pp. 965-970, Chem. Abst. 93: 89294.

Nakamura et al., "New Caries Activity I in Vitro Test of the Test Solution S-3105", Koku Eisei Gakkai Zasshi 30(4), 1980, pp. 376-381, Chem. Abst. 94: 135357h.

Emilson et al., "Growth of *Streptococcus mutans* on Various Selective Media", Journal of Clinical Medicine 4(1), (1976), pp. 95-98, Abst.

Sudo et al., "Model System for Studying Colonization and Growth of Bacteria on a Hydroxyapatite Surface", Infection and Immunity 12(3), (1975), pp. 576-585.

Otake et al., "Virulence of *Streptococcus mutans*: Characterization of a Serotype g Antigen Defective Mutant and its Revertants", Infection and Immunity 31(1), (1980), pp. 151-159.

Skinner et al., "Influence of Sugar Type on the Pattern of Acid Production by *Streptococcus mutans*", Journal of Dental Research 51(4), (1972), pp. 1022-1024.

*Primary Examiner*—Thomas G. Wiseman
*Assistant Examiner*—John E. Tarcza
*Attorney, Agent, or Firm*—Sandra M. Person; Gary M. Nath

[57] ABSTRACT

A medium for the selective growth and identification of *Streptococcus mutans* bacteria is disclosed, that includes a tryptone-glucose extract agar, monobasic and dibasic potassium phosphate, yeast extract, agar, a color indicator for the bacteria and a solution of sucrose ranging in concentration from 1% to 15%. Preferably, the concentration of the sucrose may range from about 3% to about 11%. A bacteria culture plate may be prepared comprising the medium, and may include a first basal layer comprised entirely of the medium, and a second overlayer agar coating, including a mixture of the medium with a calcium phosphate suspension. Both the basal layer and the overlayer agar coating are preferably adjusted to a mildly basic pH.

The present medium, and bacteria culture plates prepared therewith, offer desired bacterial specificity with no growth inhibition, that is usually the case with specific media of this kind. The present medium and bacteria culture plate is particularly useful, as *Streptococcus mutans* is considered to be instrumental in dental caries development.

47 Claims, No Drawings

MEDIUM FOR DIFFERENTIATING STREPTOCOCCUS MUTANS

BACKGROUND OF THE INVENTION

1. Field of the Invention

The present invention relates to the identification of specific strains of bacteria, and more particularly to the differentiation and identification of a variety of bacteria believed to play a role in dental caries formation.

2. Description of the Prior Art

Numerous studies conducted over close to sixty years, have determined that certain bacteria, and in particular the bacterium *Streptococcus Mutans*, are found in the oral cavity, and more particularly in association with dental surfaces, so that a linear association between the presence of this bacterium and the incidence of dental caries has evolved. *Streptococcus Mutans* is classified as acidogenic and is found in dental plaque, that forms on tooth surfaces, and is believed to participate in the decalcification of the tooth that results from the solubilization of the complex calcium hydroxyphosphate, known as hydroxyapatite. Thus, areas where caries formation is noted, frequently exhibit a pH in the acid range.

While studies have not conclusively established the role that the various bacteria, including *Streptococcus Mutans* play in caries formation, further efforts at investigation and examination of *Streptococcus Mutans*, have been hampered by the inability to isolate and enumerate this bacteria in samples of human dental plaque. A variety of culture media have been proposed and tested, for the purpose of selectively isolating *Streptococcus Mutans*, however the results obtainable with the various culture media have been inconsistent and in some instances contradictory to the initial experiments where such media were tested and disclosed for use. For example, Gold et al., (1973, Arch. Oral Biol., 18:1357–1364), proposed a selective medium utilizing Mitis-Salivarius agar with added sucrose and bacitracin (MSB), however this medium and nine others were comparatively tested by Little et al. (1977, J. Clin, Microbiol., 5:578–583), and MSB gave lower microbial counts of this organism, than other non-selective media also tested. One of the media comprised a dilute trypticase yeast extract known as MM10SB, based upon a medium described and tested by Loesche et al. (1972, Arch. Oral Biol., 17:1311), as a non-selective gross medium for a variety of oral organisms.

Additional specific media have been developed and tested, however to the same results as described above. In particular Keele et al. (1973, J. Dent. Res., 52:1054), disclose a medium utilizing plate count agar, monobasic and dibasic potassium phosphate, yeast extract, BCP indicator and 1% glucose (GAM), which in turn, was derived from a medium disclosed by Handleman et al. (1968, Arch. Oral Biol., 13:1187–1196), that had sought to specify acidogenic streptococci by the use of tryptone-glucose agar, monobasic and dibasic potassium phosphate, yeast extract and BCP indicator. Both of these media, however, while offering generally uninhibited growth, are inadequately specific to differentiate *Streptococcus Mutans*, to the extent necessary and desirable to permit further observation and experimentation to be made.

A need therefore exists for the development of a culture medium that is specific for differentiation of *Streptococcus Mutans* without inhibiting the development of full bacterial counts.

SUMMARY OF THE INVENTION

In accordance with the present invention, a medium for the selective growth and identification of *Streptococcus Mutans* bacteria is disclosed, which consists essentially of a tryptone-glucose extract agar, monobasic and dibasic potassium phosphate, yeast extract, agar, a color indicator for said bacteria, and a solution of sucrose ranging in concentration from 1% to 15%. Preferably, the solution concentrations of the added sucrose may range from about 3% to about 11%, and more particularly, a 5% solution may be utilized herein.

The present invention also includes a bacterial culture plate comprising the medium of the present invention disposed as a first basal layer in a standard receptacle or petri dish, and an overlayer agar coating comprising a mixture of a calcium phosphate suspension and a sterile quantity of the medium of the present invention, adjusted to a mildly basic pH.

A method for the enumeration of *Streptococcus Mutans* bacteria from dental plaque samples is also disclosed and comprises preparing liquid dilutions of dispersed dental plaque samples containing a mixture of numerous types of said bacteria, and disposing predetermined quantities of said liquid dilutions on one or more of the plates of the present invention. The plates are then incubated in accordance with conventional procedures, after which the resulting distinctive colonies of *Streptococcus Mutans* may be identified and counted among the colonies of other types of bacteria.

The medium of the present invention, herein designated sucroseacidogen medium (SAM), demonstrates a substantially improved specificity for *Streptococcus Mutans* bacteria, that offers improved identification and observation of *Streptococcus Mutans* colonies from human plaque samples. Also, the medium does not inhibit colony growth, and favorably increased bacterial numbers are obtained compared to selective media that also facilitates experimental observation of bacterial activity. Results utilizing the present medium were thus comparable to results that would be expected and are obtained with pure bacterial cultures.

Accordingly, it is a principal object of the present invention to provide a culture medium for the growth and identification of the bacterium *Streptococcus Mutans*.

It is a further object of the present invention to provide a medium as aforesaid, which shows improved specificity and full bacterial counts for the desired bacterium.

It is a yet further object of the present invention to provide a culture plate utilizing the medium of the present invention.

It is a yet further object of the present invention to provide a culture plate as aforesaid that facilitates the exclusive identification of the acidogenic properties of *Streptococcus Mutans* bacteria.

Other objects and advantages will become apparent to those skilled in the art from a review of the ensuing detailed description.

DETAILED DESCRIPTION

In accordance with the present invention, a medium for selectively differentiating the bacteria *Streptococcus Mutans* consists essentially of a tryptone-glucose extract agar, monobasic potassium phosphate, dibasic potassium phosphate, yeast extract, a standard agar, the color indicator bromcresol purple, and a quantity of a sucrose solution, varying in concentration from about 1% to about 15%.

Tryptone-glucose extract agar is a well known component of culture media, and is preferably present in an amount of 2.35%. Both monobasic and dibasic potassium phosphate are respectively in amounts of about 0.12%. In addition, the yeast extract is present and is utilized in an amount of about 0.25%, a standard agar is used in an amount of 0.5% while an indicator such as bromcresol purple, is utilized in an amount of about 0.0032%.

The foregoing percentages are generally conventional, and conform in amount to culture media disclosed and utilized in the prior art discussed earlier herein, the pertinent portions of which are incorporated herein by reference.

The present invention relates primarily to the employment of sucrose in an amount ranging from about 1% to about 15%, in place of the carbohydrate glucose, previously utilized and discussed in the Keele et al. article. Preferably, sucrose is utilized in a concentration that ranges from about 3% to about 11%, and more particularly at a concentration of 5%.

Sucrose is a disaccharide that upon hydrolysis generally yields glucose and fructose. Sucrose has been utilized previously, as indicated by Gold et al., discussed earlier, however numbers of colonies of *Streptococcus Mutans* have been reduced compared to non-selective media. Likewise, the use of glucose, a monosaccharide in the medium disclosed by Keele et al. proved similarly deficient, in that, while sufficient numbers of bacteria were developed, differentiation was lacking and identification was therefore made difficult.

Accordingly, the present medium may be utilized in the preparation of a bacterial culture plate, also a part of the present invention. The culture plate comprises a receptacle into which a first basal layer may be disposed, the basal layer comprising a quantity of the present medium. An overlayer agar coating is utilized on top of the basal layer, and comprises a mixture of a suspension of calcium phosphate, and a sterile quantity of the medium. The suspension of calcium phosphate is preferably prepared by passing a quantity of calcium chloride through a filter medium, and thereafter passing through such medium a quantity of potassium hydrogen phosphate. For example, a quantity of $CaCl_2$ and one-half the volumetric quantity of $K_2HPO_4$ may be sequentially passed through a microfilter, i.e. having a pore size of 0.45 $\mu$m, and into a sterile container, to form the calcium phosphate suspension. The overlayer agar coating may then be prepared by mixing a quantity of the suspension with a quantity of the medium of the present invention. For example, 100 parts per volume of the medium may be mixed with 15 parts per volume of the suspension to prepare the overlayer agar coating.

Generally, the present bacterial culture plate is prepared with the basal layer larger than the overlayer agar coating. While the specific amount of each component are not critical, the basal layer and the overlayer agar coating may be present in the receptacle of the culture plate in a volumetric ratio with respect to each other ranging up to about 3:1. Thus, for example, in the instance where 100×15 mm petrie dishes serve as the receptacles, the basal layer may be formed by dispensing 15 milliliters of the medium into the petrie dish, after solidification of which, 5 milliliters of the overlayer agar coating may be dispensed on the upper disposed surface of the basal layer.

Additionally, the respective components of the bacterial culture plate of the present invention are adjusted in pH to a mildly basic state. This assures the stability of the culture plate, as the premature solubilization of the calcium phosphate in the overlayer agar coating is inhibited. Preferably, the pH of both components is adjusted to between 7.0 and 8.0, and more particularly, usually ranges from 7.4 to 7.5.

The invention includes a method for preparing the medium utilized in the preparation of both the basal layer and the overlayer agar coating. The method comprises preparing a mixture that consists essentially of the ingredients of the present medium, as set forth earlier, adjusting such mixture to a mildly basic pH, generally within the range of pH stated above. Adjustment of the pH may be accomplished by use of conventional compound such as sodium hydroxide and hydrochloric acid. For example, a pH adjustment may be made by the addition of a quantity of 1N sodium hydroxide until the pH ranges about 7.4. In the instance where pH must be lowered, 1N hydrochloric acid may be utilized in similar regard. Generally, small amounts of either or both additives are required to stabilize the pH of the medium.

pH adjustment of the overlayer agar coating may be made both after the coating is prepared, and during the preparation of its individual components. Accordingly, the preparation of calcium phosphate suspension may include the adjustment of pH to the mildly basic range specified above, by the addition of a quantify of, for example, 10N sodium hydroxide. Similarly, the portion of the coating attributable to the mixture, may also be individually adjusted in pH prior to its combination with the suspension. Thereafter, adjustment of the overlayer agar coating may again be made following the mixture of the two components. The object of pH adjustment, is to maintain a uniform mildly basic pH throughout the contents of the bacterial culture plate.

As noted above, the preparation of the medium is complete when the pH-adjusted mixture is sterilized. Sterilization may be performed by routine techniques, utilizing apparatus such as a steam auto clave, all as well known in the art. After sterilization, the now liquid, heated medium may be removed, for direct participation in the preparation of a bacterial culture plate, or for storage for future use.

In the instance where preparation of the bacterial culture plate is directly contemplated, the heated, sterilized medium is cooled to a temperature that may range from about 50° C. to about 55° C., and a quantity of the medium is thereafter dispensed into one or more appropriate receptacles. As mentioned earlier, a 100×15 mm petrie dish may be provided with approximately 15 ml of the medium in this condition.

A further quantity of the medium at this temperature may be combined with the calcium phosphate suspension, in the range of amounts and in the manner described earlier, to form the overlayer agar coating. After combination of the two components of the overlayer agar coating, and the adjustment of the pH of this resulting component to the mildly basic range, a quantity of the overlayer agar coating may be dispensed over the basal layer, subsequent to the solidification of the latter. For example, 5 ml of the overlayer agar coating may be disposed over the basal layer formed by the earlier addition of 15 ml of the medium to the petrie dish.

After the respective components of the culture plate have been dispensed, the plate is allowed to solidify and is thereafter preferably dried prior to use by conventional practice, such as by incubation. Generally, incubation is conducted at room temperature, and may preferably be conducted at a temperature of about 37° C. for a period of about 24 hours. The parameters of incubation may vary, and the invention is not limited to a specific set of conditions.

The method for the recovery of *Streptococcus Mutans* bacteria from dental plaque comprises preparing liquid dilution of the dispersed plaque sample and innoculating one or more of the bacterial culture plates prepared in accordance herewith. The innoculated plates are then incubated in accordance with standard procedures, and thereafter colony counts may be conducted, to determine the numbers and structure of the bacteria that have grown thereon. Generally, incubation is conducted for a period of time of up to about 5 days, and usually takes place under anaerobic atmospheric conditions and a temperature of 37° C.

As noted earlier, the advantages of the present invention, are that the specific strains of *Streptococcus Mutans* form raised, irregular and distinct colonies that are further identifiable by their tendency to exhibit a yellow color. In an exclusive, identifiable manner, these particular bacterial strains solubilize the calcium phosphate located in the overlayer agar coating, and thereby form a substantially transparent ring around the colony. Other strains of bacteria do not present this appearance so that the *Streptococcus Mutans* may be clearly identified. Moreover, the medium promotes the full growth of *Streptococcus Mutans* colonies so that numbers available for identification and analysis are equivalent to those on other non-selective media.

The present invention will be better understood from a consideration of the following illustrative examples. All percentages are by weight unless otherwise specified.

EXAMPLE 1

A series of bacteria culture plates were prepared as follows: a quantity of the present culture medium was prepared from 2.35% tryptone glucose extract agar, 0.12% monobasic potassium phosphate, 0.12% dibasic potassium phosphate, 0.25% yeast extract, 0.5% regular agar, 0.0032% bromcresol purple, and 5.0% sucrose. The foregoing ingredients were mixed with each other, and the resulting mixture was adjusted to a pH of 7.4 with 1N sodium hydroxide. Thereafter, the mixture was sterilized in an autoclave, and, after its removal, cooled to a temperature of from about 55° C. to about 60° C. Thereafter, 15 ml portions of the mixture were dispensed to a series of 100×15 mm petrie dishes, to form the basal layer. The petrie dishes were allowed to stand so that the basal layer solidified.

A sterile calcium phosphate suspension was prepared by sequentially passing 100 ml of 10% calcium chloride and 50 ml of 10% dibasic potassium phosphate through a microfilter having a pore size of 0.45 μm. The filtrate was directed into a sterile container and a calcium phosphate suspension resulted. The suspension was adjusted to a pH of 7.4 with 10N sodium hydroxide, and 15 ml of the suspension was thereafter added to an additional 100 ml of the medium prepared earlier, that had been held at 50° C., to form a calcium phosphate-containing overlayer agar. The pH of this overlayer agar was aseptically adjusted to 7.4, by adding, when necessary, either 1N sodium hydroxide or 1N hydrochloric acid. 5 mls of the overlayer agar were then disposed on the free surface of the solidified basal layer of each petrie dish so prepared, and the resulting overlayer agar coating was allowed to solidify. The plates thus prepared were dried prior to their use by incubation for 24 hours at 37° C.

EXAMPLE 2

Comparative testing was conducted with a series of bacterial culture plates prepared with a variety of media in addition to the plates prepared in Example 1, above. The plates prepared for comparison with the present invention were as follows:

A. A non-selective medium disclosed in the Loesche et al. article, referred to earlier herein, and incorporated herein by reference, this medium known as MM10-S.

B. A medium similar to the present invention, with the difference that glucose was utilized in place of sucrose; this medium known hereinafter as GAM.

C. A medium routinely employed for the selective recovery of *Streptococcus Mutans*, and defined in Gold et al., cited earlier and incorporated herein by reference, comprising a Mitis-Salivarius agar having added sucrose and bacitracin, hereinafter known as MSB.

D. Lactobacillus Selection Agar utilized for the selective recovery of lactobacilli, hereinafter identified as LBS,BBL.

The above-identified media and the medium of the present invention, identified herein as SAM, were each inoculated in duplicate plates from overnight broth cultures of several strains of oral microorganisms that had been diluted in phosphate-buffered saline to yield approximately $10^4$–$10^5$ colony forming units per milliliter (CFU/ml). The samples were spiral plated, and the respective innoculated plates were incubated anaerobically for five days at a temperature of 37° C.

After incubation was complete, colony counts were determined for each organism on each type of medium.

The recoveries and resulting colony counts for the various strains of *Streptococcus Mutans* were comparable for the medium identified as MM10-S and the medium of the present invention. The colony forming units per milliliter noted with respect to the MSB medium were lower than those of MM10-S, GAM and the medium of the present invention, for all *Streptococcus Mutans* strains tested. While *Streptococcus Sanguis* and *Lactobacillus Casei* grew well on the medium of the present invention, they could nonetheless be distinguished readily from *Streptococcus Mutans*, by colony morphology. Also, organisms capable of acidifying the medium of the present invention to a pH of 4.5 or less produced a zone of clearing around each colony that indicated solubilization of the calcium phosphate suspension in the overlayer agar coating. Of the organisms tested, only *Streptococcus Mutans* produced this zone of clearing, so that present medium and the bacteria culture plate produced therewith, provided the necessary specificity for identification and study of this bacterium.

EXAMPLE 3

Additional bacterial culture plates were prepared as discussed in Examples 1 and 2 to compare results of innoculation with mixed cultures of plaque bacteria containing *Streptococcus Mutans*. The media prepared in two bacteria culture plates and thereafter tested comprised the medium of the present invention, MM10-S and MSB. As with the tests reported above, counts of *Streptococcus Mutans*, on the medium of the present invention and on MM10-S were similar while counts reported on MSB were lower. The cultures of initial *Streptococcus Mutans* were derived from dental plaque samples, and it was found that the lower numbers of *Streptococcus Mutans* present in some of the plaque samples were reliably counted on the medium of the present invention, but could not be counted in such way on the MM10-S medium. The MM10-S medium produced much higher background counts of plaque organisms other than *Streptococcus Mutans*, and thus tended to obscure the colonies of this organism.

The results of the above tests suggest that the medium of the present invention offers an improved vehicle for the identification and counting of *Streptococcus Mutans* in dental plaque, as it provides for the growth of easily discernible colonies of this organism, without the reduction in numbers that often occurs on selective media.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method for the selective identification of *Streptococcus mutans* comprising:
   A. preparing a medium consisting essentially of:
      1. tryptone-glucose extract agar;
      2. dibasic potassium phosphate;
      3. monobasic potassium phosphate;
      4. yeast extract;
      5. agar;
      6. a color indicator for said bacteria; and
      7. from about 1% to about 15% sucrose;
   B. placing a quantity of said medium in a receptacle to form a first basal layer;
   C. permitting said first basal layer to solidify;
   D. preparing an overlayer agar coating comprising a mixture of a suspension of calcium phosphate, and a sterile quantity of said medium;
   E. disposing a quantity of said overlayer agar coating on said first basal layer to form a product, wherein the amount of calcium phosphate is sufficient to detect production of acid by *Streptococcus Mutans*.
   F. drying the product to form a culture plate ready for use;
   G. inoculating and incubating under conditions suitable for growth the culture plate with a sample to be determined; and
   H. Observing the incubated plate to identify *Streptococcus Mutans*.

2. The method of claim 1 wherein said sucrose ranges in concentration from about 3% to about 11% by weight.

3. The method of claim 2 wherein said sucrose is present in a concentration of 5 wt. %.

4. The method of claims 1, 2 or 3 wherein said tryptone-glucose extract agar is present in an amount of 2.35 wt. %, said monobasic potassium phosphate is present in an amount of 0.12 wt. %, said dibasic potassium phosphate is present in an amount of 0.12 wt. %, said yeast extract is present in an amount of 0.25 wt. %, and said agar is present in an amount of 0.5 wt. %.

5. The method of claim 4 wherein said indicator comprises bromcresol purple.

6. The method of claim 5 wherein said indicator is present in an amount of 0.0032 wt. %.

7. The method of claim 4 wherein said suspension comprises a filtered mixture of calcium chloride and potassium hydrogen phosphate.

8. The method of claim 1 wherein said suspension is prepared by sequentially passing said calcium chloride and said potassium hydrogen phosphate through a filter medium, and into a sterile container.

9. The method of claim 4 wherein the mixture of said overlayer agar coating comprises 100 parts by volume of said medium and 15 parts by volume of said suspension.

10. The method of claim 4 wherein said basal layer and said overlayer agar coating are disposed in said receptacle, in a volumetric ratio with respect to each other ranging up to about 3:1.

11. The method of claim 4 wherein said basal layer and said overlayer agar coating are individually adjusted to a mildly basic pH.

12. The method of claim 11 wherein said mildly basic pH comprises a pH ranging between 7.0 and 8.0.

13. The method of claims 1, 2 or 3 wherein said indicator comprises bromcresol purple.

14. The method of claim 13 wherein said indicator is present in an amount of 0.0032 wt. %.

15. The method of claims 1, 2 or 3 wherein said suspension comprises a filtered mixture of calcium chloride and potassium hydrogen phosphate.

16. The method of claims 1, 2 or 3 wherein the mixture of said overlayer agar coating comprises 100 parts by volume of said medium and 15 parts by volume of said suspension.

17. The method of claims 1, 2 or 3 wherein said basal layer and said overlayer agar coating are disposed in said receptacle, in a volumetric ratio with respect to each other ranging up to about 3:1.

18. The method of claims 1, 2 or 3 wherein said basal layer and said overlayer agar coating are individually adjusted to a mildly basic pH.

19. The method of claim 18 wherein said mildly basic pH comprises a pH ranging between 7.0 and 8.0.

20. A bacterial culture plate for the selective differentiation of *Streptococcus Mutans* bacteria comprising:
   A. a receptacle;
   B. a first basal layer comprising a medium, said medium consisting essentially of:
      1. tryptone-glucose extract agar;
      2. dibasic potassium phosphate;
      3. monobasic potassium phosphate;
      4. yeast extract;
      5. agar;
      6. a color indicator for said bacteria; and
      7. from about 1% to about 15% by weight of sucrose;
   C. an overlayer agar coating disposed over said first basal layer, said overlayer agar coating comprising a mixture of a suspension of calcium phosphate, and a sterile quantity of said medium wherein the amount of calcium phosphate is sufficient to detect production of acid by *Streptococcus Mutans*.

21. The bacterial culture plate of claim 20 wherein said sucrose ranges in concentration from about 3% to about 11% by weight.

22. The bacterial culture plate of claim 21 wherein said sucrose is present in a concentration of 5% by weight.

23. The bacterial culture plate of claims 20, 21 or 22 wherein said tryptone-glucose extract agar is present in an amount of 2.35 wt. %, said monobasic potassium phosphate is present in an amount of 0.12 wt. %, said dibasic potassium phosphate is present in an amount of 0.12 wt. %, said yeast extract is present in an amount of 0.25 wt. %, and said agar is present in an amount of 0.5 wt. %.

24. The bacterial culture plate of claim 23 wherein said indicator comprises bromcresol purple.

25. The medium of claim 24 wherein said indicator is present in an amount of 0.0032 wt.%.

26. The bacterial culture plate of claim 25 wherein said mixture comprises 100 parts by volume of said medium and 15 parts by volume of said suspension.

27. The bacterial culture plate of claim 25 wherein said basal layer and said overlayer agar coating are present in said receptacle, in a volumetric ratio with respect to each other ranging up to about 3:1.

28. The bacterial culture plate of claim 25 wherein said basal layer and said overlayer agar coating are adjusted to a mildly basic pH.

29. The bacterial culture plate of claim 23 wherein said mixture comprises 100 parts by volume of said medium and 15 parts by volume of said suspension.

30. The bacterial culture plate of claim 23 wherein said basal layer and said overlayer agar coating are present in said receptacle, in a volumetric ratio with respect to each other ranging up to about 3:1.

31. The bacterial culture plate of claim 30 wherein said basal layer and said overlayer agar coating are adjusted to a mildly basic pH.

32. The bacterial culture plate of claim 23 wherein said basal layer and said overlayer agar coating are adjusted to a mildly basic pH.

33. The bacterial culture plate of claims 20, 21 or 22 wherein said indicator comprises bromcresol purple.

34. The bacterial culture plate of claim 33 wherein said indicator is present in an amount of 0.0032 wt.%.

35. The bacterial culture plate of claim 34 wherein said mixture comprises 100 parts by volume of said medium and 15 parts by volume of said suspension.

36. The bacterial culture plate of claim 34 wherein said basal layer and said overlayer agar coating are adjusted to a mildly basic pH.

37. The bacterial culture plate of claim 33 wherein said mixture comprises 100 parts by volume of said medium and 15 parts by volume of said suspension.

38. The bacterial culture plate of claim 33 wherein said basal layer and said overlayer agar coating are present in said receptacle, in a volumetric ratio with respect to each other ranging up to about 3:1.

39. The bacterial culture plate of claim 33 wherein said basal layer and said overlayer agar coating are adjusted to a mildly basic pH.

40. The bacterial culture plate of claims 20, 21 or 22 wherein said suspension comprises a filtered mixture of calcium chloride and potassium hydrogen phosphate.

41. The bacterial culture plate of claims 20, 21 or 22 wherein said mixture comprises 100 parts by volume of said medium and 15 parts by volume of said suspension.

42. The bacterial culture plate of claim 41 wherein said basal layer and said overlayer agar coating are present in said receptacle, in a volumetric ratio with respect to each other ranging up to about 3:1.

43. The bacterial culture plate of claim 41 wherein said basal layer and said overlayer agar coating are adjusted to a mildly basic pH.

44. The bacterial culture plate of claims 20, 21 or 22 wherein said basal layer and said overlayer agar coating are present in said receptacle, in a volumetric ratio with respect to each other ranging up to about 3:1.

45. The bacterial culture plate of claim 44 wherein said basal layer and said overlayer agar coating are adjusted to a mildly basic pH.

46. The bacterial culture plate of claims 20, 21 or 22 wherein said basal layer and said overlayer agar coating are adjusted to a mildly basic pH.

47. The bacterial culture plate of claim 46 wherein said mildly basic pH comprises a pH ranging between 7.0 and 8.0.

* * * * *